(12) United States Patent
Yang et al.

(10) Patent No.: US 8,309,689 B2
(45) Date of Patent: Nov. 13, 2012

(54) HIGH YIELD DIALYSIS-FREE PROCESS FOR PRODUCING ORGANOSOLUBLE REGENERATED SILK FIBROIN

(75) Inventors: Jen-Chang Yang, Taipei (TW); Sheng-Yang Lee, Taipei (TW); Chien Chung Chen, Taipei (TW); Yun-Ting Hsu, Taipei (TW); Hong-Da Wu, Taipei (TW); Dian-Yu Ji, Taipei (TW)

(73) Assignee: Taipei Medical University, Taipei (TW)

( * ) Notice: Subject to any disclaimer, the term of this patent is extended or adjusted under 35 U.S.C. 154(b) by 232 days.

(21) Appl. No.: 12/783,818

(22) Filed: May 20, 2010

(65) Prior Publication Data

US 2011/0288273 A1    Nov. 24, 2011

(51) Int. Cl.
  *C07K 1/30* (2006.01)
(52) U.S. Cl. ........................................................ 530/353
(58) Field of Classification Search .................... 530/353
  See application file for complete search history.

(56) References Cited

U.S. PATENT DOCUMENTS 4,233,212 A * 11/1980 Otoi et al. ...................... 530/353
5,252,285 A    10/1993 Lock
6,110,590 A     8/2000 Zarkoob et al.
7,285,637 B2   10/2007 Armato et al.
2007/0187862 A1  8/2007 Kaplan et al.

OTHER PUBLICATIONS

Ha, Sung-Won, et al, "Dissolution of *Bombyx mori* Silk Fibroin in the Calcium Nitrate Tetrahydrate-Methanol System and Aspects of Wet Spinning of Fibroin Solution," Biomacromolecules, 2003, 4, pp. 488-496.

Phillips, David M., et al., "Dissolution and Regeneration of *Bombyx mori* Silk Fibroin Using Ionic Liquids," Journal of the American Chemical Society, 2004, 126, pp. 14350-14351.

* cited by examiner

*Primary Examiner* — Chih-Min Kam
(74) *Attorney, Agent, or Firm* — McDonnell Boehnen Hulbert & Berghoff LLP

(57) ABSTRACT

The invention relates to a simple and high yield process for producing a regenerated silk fibroin which does not need dialysis. Particularly, a process of the invention is characterized in that the silk fibroin is precipitated by applying a shear stress and/or changing the solvent power of the fibroin solution. The process of the invention simplifies the process of producing silk fibroin and greatly shortens the process time to 1 to 2 hours, whereas the conventional dialysis process is complex and needs around 2 to 3 days. In addition to reducing the time needed, the process of the invention can increase productivity of silk fibroin by at least 8%.

31 Claims, 1 Drawing Sheet

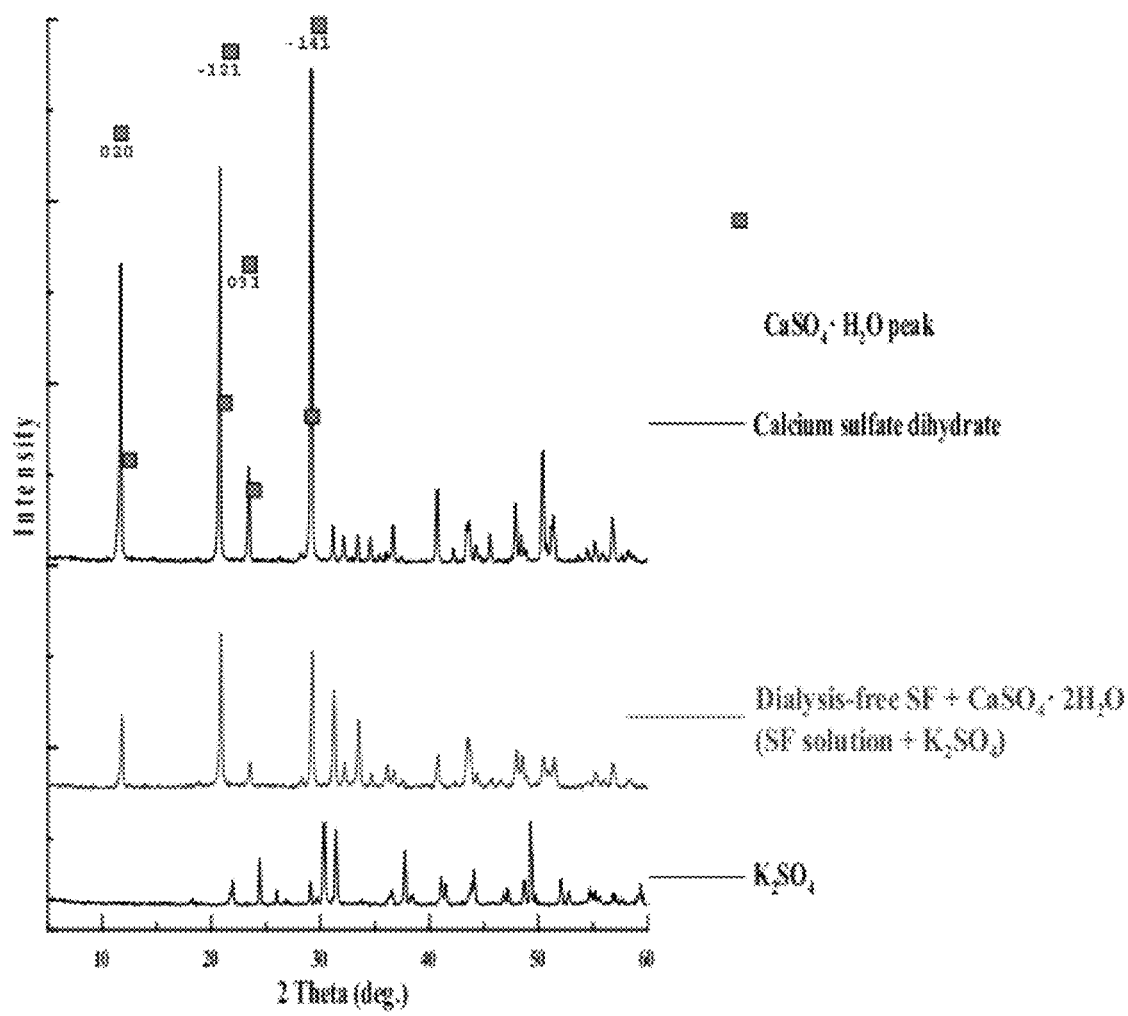

HIGH YIELD DIALYSIS-FREE PROCESS FOR PRODUCING ORGANOSOLUBLE REGENERATED SILK FIBROIN

FIELD OF THE INVENTION

The invention provides a simple and high yield process for producing a regenerated silk fibroin which does not need dialysis. Particularly, the process of the invention is characterized in that the silk fibroin is precipitated by applying a shear stress to it.

BACKGROUND OF THE INVENTION

Silk protein is regarded as a natural biomaterial, and developments of new uses of silk threads in various fields other than that of clothing are underway. Silk fibroin has very good properties such as high strength and flexibility, biocompatibility, blood compatibility, water permeability and oxygen permeability, so it can be used in surgery as implant material and in tissue engineering applications. In addition, silk fibroin can be used as a cell culture matrix, as a substratum for cultivation of cells, as a burn wound dressing membrane, as an enzyme-immobilization material, and in an oral dosage form.

Silk is mainly composed of fibroin and sericin, and the fibroin has 19% hydrophilic side chains containing a heavy chain with a molecular weight of 325 kD (45% glycine, 30% alanine, 12% serine) and a light chain with a molecular weight of 25 kD (15% asparate, 11% glycine, 14% alanine, 11% serine). In addition, the sericin in silk fibers is in an amount of around 25% by weight and it has 76% hydrophilic side chains. The sericin will cause inflammation, so the silk fibers should be degummed with hot water containing surfactants before medical applications. Fibrous products based on silk fibroins have excellent mechanical properties. Nevertheless, silk fibroin has Tg ranging from 170-175° C. and the temperature of transiting random-coil to β-structure conformation is 212° C. Therefore, when the temperature rises to 280° C., the silk fibroin will start to cleave. Thus, silk fibroin is usually processed by solution process rather than by melt process.

To conduct the solution process, silk fibroin need to be dissolved in a salts containing aqueous solution first. U.S. Pat. No. 5,252,285 indicates that fibroin is known to be soluble in certain high ionic strength aqueous salt solutions, for example, aqueous lithium thiocyanate (LiSCN), sodium thiocyanate (NaSCN), calcium thiocyanate ($Ca(SCN)_2$), magnesium thiocyanate ($Mg(SCN)_2$), calcium chloride ($CaCl_2$), lithium chloride (LiCl), lithium bromide (LiBr), zinc chloride ($ZnCl_2$), magnesium chloride ($MgCl_2$), copper salts such as copper nitrate ($Cu(NO_3)_2$), copper ethylene diamine ($Cu(NH_2CH_2CH_2NH_2)_2(OH)_2$) and $Cu(NH_3)_4(OH)_2$ and Ajisawa's reagent ($CaCl_2$/ethanol/water). The processing of silk fibroin solution is difficult due to salt concentration increasing when solvent evaporates at an elevated temperature. Even after the salts removed by dialysis out of such aqueous salt/fibroin solutions, the concentration of this fibroin solution is usually too dilute to spin fiber threads. More commonly, the organosoluble silk fibroin is first harvested by freeze drying process from the dialyzed solution. Then, fibers can be spun from fibroin solution dope that was prepared by dissolved silk fibroin solution in an organic solvent. US 2007/0187862 A1 provides for concentrated aqueous silk fibroin solutions and an all-aqueous mode for preparation of concentrated aqueous fibroin solutions by dialysis that avoids the use of organic solvents, direct additives, or harsh chemicals. This application indicates that dialysis of the solution against a hygroscopic polymer is also sufficient to control water content in the formation of silk hydrogels.

Concerning the bottleneck of silk fibroin mass-production, the dialysis process is usually time-consuming and difficult to scale up. Moreover, during the dialysis procedure, the intermolecular hydrogen bonds of silk fibroins gradually form, so molecules of silk fibroins tend to form crystals where the second structure of silk fibroin gradually becomes silk crystal form I (organic solvent soluble) and silk crystal form II (organic solvent insoluble) from random-coil conformation. Furthermore, gelation of silk fibroin renders its second structure unstable, so the solubility of regenerated silk fibroin is hard to maintain.

Sung-Won Ha et al. dissolves silk fibroin with the calcium nitrate tetrahydrate-methanol system and uses wet spinning method to spin regenerated fibroin fiber (Biomacromolecules, 2003, 4 (3), pp 488-496). A solvent system is developed to use a solution containing 1-butyl-3-methylimidazolium chloride as solvent, which can dissolve silk fibroin without dialysis process (Phillips, D. M.; Drummy, L. F.; Conrady, D. G.; Fox, D. M.; Naik, R. R.; Stone, M. O.; Trulove, P. C.; De Long, H. C.; Mantz, R. A. *Journal of the American Chemical Society*, 2004, 126, 14350-14351). However, this solvent system is expensive and is not appropriate for industrial production. U.S. Pat. No. 7,285,637 applies a formic acid solution containing a small amount of salts to break the disulfide bonds between heavy (350 kDa) and light (27 kDa) chains of silk fibroin so that the dissolution of the silk fibroin in the solution can be facilitated. Nevertheless, there is a serious molecular chain cleavage of silk fibroin in the solvent system. Furthermore, it was reported that silk fibroin can dissolve in hexafluoroisopropanol solvent after 5 months (Zarkoob, S.; Reneker, D. H.; Ertley, D.; R. K. Eby; Hudson, S. D. Synthetically spun silk nanofibers and a process for marking the same, 6110590, 2000). The long dissolving time makes the method impractical for mass production.

Therefore, there is still a need to develop a more convenient and efficient process for producing a silk fibroin.

SUMMARY OF THE INVENTION

The invention provides a process of producing a regenerated silk fibroin, comprising the steps of:
  (a) dissolving degummed silk fibroins in a salt containing solution to give a fibroin solution; and
  (b) applying a shear stress to the fibroin solution for a time sufficient to make the silk fibroin precipitate, thereby producing a regenerated silk fibroin.

The invention further provides a process of producing a regenerated silk fibroin, comprising the steps of:
  (a) dissolving degummed silk fibroins in a salt containing solution to give a fibroin solution;
  (b') changing the solvent power of the fibroin solution; and
  (c) applying a shear stress to the fibroin solution to the fibroin solution for a time sufficient to make the silk fibroin precipitate, thereby producing a regenerated silk fibroin.

BRIEF DESCRIPTION OF THE DRAWINGS

FIG. 1 shows the XRD results of the calcium sulfate dihydrate ($CaSO_4.2H_2O$), the fibroin along with the calcium sulfate dihydrate ($CaSO_4.2H_2O$) produced by the process according to the invention, and the potassium sulfate.

DETAILED DESCRIPTION OF THE INVENTION

The invention relates to a simple and high yield process for producing a dialysis-free regenerated silk fibroin by changing phase equilibrium. The phase equilibrium can be changed by, for example, applying a shear stress or changing solvent power. Various means of changing phase equilibrium can be used in combination to increase the precipitation rate. The process of the invention simplifies the process of producing silk fibroin and greatly shortens the processing time to 1 to 2 hours, whereas the dialysis process is complex and needs around 2 to 3 days. In addition to reducing the time needed, the process of the invention can increase productivity of silk fibroin by at least 8%.

In one aspect, the invention provides a process of producing a regenerated silk fibroin, comprising the steps of:
(a) dissolving degummed silk fibroins in a salt containing solution to give a fibroin solution; and
(b) applying a shear stress to the fibroin solution for a time sufficient to make the silk fibroin precipitate, thereby producing a regenerated silk fibroin.

In another aspect, in addition to the application of shear stress, the process can further comprise a step of changing the solvent power to increase the precipitation rate. The dissolution of silk fibroin is correlated with the power of the solvent in the solution. Silk fibroin dissolves more easily when the power of the solvent is weak, and vice versa. The power of the solvent in the solution, in turn, is correlated with the proportion of the components in the solvent. Therefore, the power of the solvent can be lowered by lowering the proportion of salts in the solution, increasing the proportion of water in the solution, or increasing the proportion of the alcohol in the solution if alcohol is included.

The term "fibroin" includes selected proteins; preferably, fibroins are obtained from a solution containing degummed silkworm silk proteins. The silkworm silk proteins are obtained, for example, from *Bombyx mori*. The silk proteins which are used to obtain the degummed silk fibroins in the process of this invention can be cocoons, raw silk, waste cocoons, raw silk waste, bisu (un-peelable cocoons), silk fabric waste, bourette, and the like. Alternatively, the silk proteins suitable for use in the present invention can be obtained from a solution containing a genetically engineered silk, such as from bacteria, yeast, mammalian cells, transgenic animals or transgenic plants. According to the invention, the term "degummed silk fibroin" refers to the silk fibroin obtained by degumming silk protein.

The term "regenerated silk fibroin" refers to the silk fibroin generated through the process of the invention.

The term "shear stress" refers to an external force acting on an object or surface parallel to the slope or plane in which it lies.

Before step (a) of the process according to the invention, the initial degumming of silk protein is done by using a treatment based on a $NaHCO_3$ solution or other degumming methods known in the art and described in the scientific literature and then the degummed silk fibroin is obtained. The term "degumming" means the partial or complete removal of sericin. The silk protein is degummed or freed from sericin by any conventional procedure. For example, it is washed in warm water containing a surface-active agent or an enzyme according to the need, and then dried.

In the dissolving step of (a) of the process of the invention, the degummed silk fibroins are dissolved in a salt containing solution.

The salt containing solution which is used in the process of this invention can comprise an aqueous cupri-ethylenediamine solution, an aqueous ammonia solution of cupric hydroxide (Schweitzer's reagent), an aqueous alkaline solution of cupric hydroxide and glycerol (Roe's reagent), an aqueous lithium bromide solution, an aqueous solution of the chloride, nitrate or thiocyanate of calcium, magnesium or zinc, and an aqueous sodium thiocyanate solution. It is preferable to use an aqueous solution of the chloride or nitrate of calcium or magnesium, because of its low cost and convenience for use. More preferably, an aqueous solution of $CaCl_2$ is used. It is more preferable to use a solution of $CaCl_2/C_2H_5OH/H_2O$ that has high ion strength (preferably in a mole ratio of 1:2:8). The concentrations of these aqueous solutions may vary according to the type of solvent used, the temperature, and the like. Where an aqueous solution of a metal salt is used, its concentration is generally 5 to 80% by weight, preferably 20 to 70% by weight, and most preferably 25 to 60% by weight.

According to the invention, the dissolution of the degummed silk fibroin in a salt containing solution can be carried out at higher temperatures, for example higher than 60° C., for 2 to 8 hours with agitation. Preferably, the dissolution is performed at a temperature of about 70° C. for 4 to 6 hours.

In step (b) of the process of the invention, a shear stress is applied to the fibroin solution to induce a phase separation so that the silk fibroin is regenerated and precipitates from the solution. According to the invention, the shear stress can be provided by stirring, homogenizer or high speed homogenizer. Preferably, 3,000 to 20,000 rpm of shear stress is provided; more preferably, 3,000 to 10,000, 5,000 to 10,000 or 5,000 to 8,000 rpm is provided.

In another aspect, the invention provides a process of producing a regenerated silk fibroin, comprising the steps of:
(a) dissolving degummed silk fibroins in a salt containing solution to give a fibroin solution;
(b') changing the solvent power of the fibroin solution; and
(c) applying a shear stress to the fibroin solution for a time sufficient to make the silk fibroin precipitate, thereby producing a regenerated silk fibroin.

In one aspect, in step (b') of the process of the invention, the solvent power of the solution can be changed by changing the proportion of the salts in the fibroin solution. In one embodiment, the solvent power is changed by lowering the proportion of salts in the solution. One or more multivalent acid ions can be added to the fibroin solution of step (a) to lower the proportion of salts in the solution by complexing the metal ion of the salt in the solution and precipitating. The multivalent acid ion is selected on the basis of the ability of the multivalent acid ion to combine with the metal ion of the salt the solution of step (a). That is, the choice of the multivalent acid ion depends on the metal ions originally contained in the fibroin solution. Preferably, the acid ion is selected from the group consisting of $SO_4^{2-}$, $C_2O_4^{2-}$, $CO_3^{2-}$, and $PO_4^{3-}$, and can be derived from a salt containing $Na^+$ and/or $K^+$. For example, the salt to give the multivalent acid ion can be $K_2SO_4$, $KHSO_4$, $Na_2SO_4$, $NaHSO_4$, $Na_3PO_4$, $Na_2HPO_4$, $NaH_2PO_4$, $K_3PO_4$, $K_2HPO_4$ or $KH_2PO_4$. Preferably, the multivalent acid salt is $K_2SO_4$. The concentration of the multivalent acid ion should be about equivalent to the concentration of the metal ions contained in the salt of the solution of step (a). By addition of the multivalent acid ions, the concentration of metal ions in the fibroin solution can be decreased, and the power of the solvent is lowered.

In one embodiment of the invention, the salt of step (a) is $CaCl_2$ or $Ca(SCN)_2$ and the multivalent acid salt to give the multivalent acid ion is $K_2SO_4$, $KHSO_4$, $Na_2SO_4$, $NaHSO_4$, $Na_3PO_4$, $Na_2HPO_4$, $NaH_2PO_4$, $K_3PO_4$, $K_2HPO_4$ or $KH_2PO_4$.

In one aspect, in step (b') of the process of the invention, the solvent power of the solution can be changed by increasing the proportion of water in the solution, for example, by adding de-ionized water to the resulting fibroin solution. Preferably, the proportion of water in the solution is more than 90 wt %, or the solution contains less than 5 wt % of fibroin. More preferably, the solution contains less than 4 wt %, 3 wt %, 2 wt % or 1 wt % of fibroin, such as 0.1 to 3 wt %, 0.1 to 2 wt %, 0.1 to 1 wt %, 0.1 to 0.99 wt % of fibroin. More preferably, the ranges of fibroin are 0.1 to 0.95 wt %, 0.5 to 0.95 wt %, 0.5 to 0.92 wt % and 0.6 to 0.9 wt %.

In one aspect, if an alcohol is included in the solution of the process of the invention as one of the solvents, the solvent power of the solution can be changed by increasing the proportion of alcohol in the solution. The alcohol can be, for example, ethanol.

After step (c) of the process of the invention, the re-generated and precipitated silk fibroin is collected and obtained. According to the invention, the harvesting of the precipitated silk fibroin can be performed by filtration. In addition, an centrifugation process can be performed optionally following the filtration in order to precipitate the silk fibroin After the harvesting step, the precipitated silk fibroin can be further washed or rinsed by deionized water to remove remaining salts and then dried to obtain regenerated silk fibroin. Preferably, the drying is freeze-drying.

The regenerated silk fibroin obtained from the process of the invention is organosoluble. The process of the invention is simple, rapid, and appropriate for mass production, and has high yield. The regenerated silk fibroin can be used in a variety of medical applications such as a drug (e.g, small molecule, protein, or nucleic acid) delivery device, including controlled release systems, wound closure systems, including vascular wound repair devices, hemostatic dressings, patches and glues, sutures, and in tissue engineering applications, such as, for example, scaffolds for tissue regeneration, ligament prosthetic devices and in products for long-term or bio-degradable implantation into the human body. The step of adding multivalent acid ion containing salt to the fibroin solution to change the solvent power of the fibroin solution can recover the metal ions used to dissolve degummed and dried silk fibroins. Particularly, when the solution containing $CaCl_2$ or $Ca(SCN)_2$ is used to dissolve degummed and dried silk fibroins, the multivalent acid ion containing salt, $K_2SO_4$, $KHSO_4$, $Na_2SO_4$, $NaHSO_4$, $Na_3PO_4$, $Na_2HPO_4$, $NaH_2PO_4$, $K_3PO_4$, $K_2HPO_4$ or $KH_2PO_4$ can be used. The acid ion of the multivalent acid salt will combine with the metal ion in the solution and precipitate. For example, $CaSO_4$ or $Ca_3(PO_4)_2$ can be formed and precipitated. Subsequently, $CaSO_4$ or $Ca_3(PO_4)_2$ can be used together with silk fibroin as bone substitute composites without removing them.

The present invention is further defined in the following examples. It should be understood that the examples, while indicating preferred embodiments of the inventions, are given by way of illustration only. From the above discussion and the examples, one skilled in the art can ascertain the essential characteristics of this invention, and can make various changes and modifications of the invention to adapt it to various uses and conditions without departing from the spirit and scope thereof.

EXAMPLES

Example 1

Preparation of Fibroin Solution

After the silkworm chrysalis was removed from the cocoon, the cocoon (30 g) was cleaned (with de-ionized water) and placed into an autoclave with de-ionized water (3,000 ml) to perform degumming. Degumming was performed at 121° C. and under pressure of 1.2 kg/cm² for 1 hour. The degummed fibroin was then cleaned with de-ionized water and dried at 50° C. for one day to yield the fibroin (20.4±0.4 g). The resulting fibroin was dissolved in $CaCl_2$/$C_2H_5OH$/$H_2O$ (mole ratio=1:2:8) to yield a solution containing 10 weight % fibroin. Stirring may be performed at 70° C. for 4 to 6 hours to fully dissolve the fibroin. The solution was then filtered through a mesh screen and spun by high speed centrifuge (5,000 rpm, 25° C.) for 20 min twice to remove the impurities.

Example 2

Preparation of Silk Fibroin by Adding Water and Applying Shear Stress

The resulting solution was then diluted (with de-ionized water) to yield a solution containing less than 1 weight % fibroin. Shear stress (by 5,000-8,000 rpm spin) and heat were then applied to the resulting solution to generate the fibroin precipitate. The fibroin was collected and cleaned to remove the salts. After being cool dried (−48° C.) for one day, fibroin powder was obtained. The yield was 87.7±3.5%. A comparative example using the fibroin solution of Example 1 but without applying shear stress to the solution shows a yield of 70.8±4.7%. Table 1 below shows the results of different ratios of the silk fibroin (SF)/($CaCl_2$/$C_2H_5OH$/$H_2O$)/diluted de-ionized water (DDW) system according to the process described above.

TABLE 1

| SF/solution system/DDW (Ratio) | Diluted Rate (w/w) | Static State (10 min) + Shear-Induced Precipitation (5 min) |
|---|---|---|
| 0.91/8.18/90.91 | 1:10 | ○ |
| 0.63/5.63/93.75 | 1:15 | ○ |
| 0.48/4.29/95.24 | 1:20 | ○ |
| 0.38/3.46/96.15 | 1:25 | ○ |
| 0.32/2.90/96.77 | 1:30 | ○ |
| 0.24/2.20/97.56 | 1:40 | ○ |
| 0.20/1.76/98.04 | 1:50 | ○ |

○: silk fibroin precipitated.

It can be learned from Table 1 that the silk fibroin can be precipitated from the solution by adding de-ionized water and by applying shear stress to the solution.

The molecular weight of silk fibroin can be indexed by inherent viscosity measurement. The regenerated SF powder was dissolved in formic acid to prepare 1 w/v % sample solution. The viscometer (Cannon Penske Routine Viscometers, Size No. 75) was filled with 10 mL sample solution at 25° C. for constant temperature. An experiment was conducted to measure the efflux time necessary for the sample solution to flow from point b to d. The value of inherent viscosity, $\eta_{inh}$, was calculated by the following equation:

$$\eta_r = \frac{\eta}{\eta_0} = \frac{\rho t}{\rho_0 t_0}$$

$$\eta_{inh} = \frac{\ln \eta_r}{C} = \frac{2.303 \log \eta_r}{C}$$

where $\eta_0$ is the viscosity of the solvent, $\eta$ is the viscosity of the sample solution, $\rho_0$ is the density of the solvent, $\rho$ is the density of the sample solution, $t_0$ is the efflux time of the solvent, t is the efflux time of the sample solution, and C is the gram of polymer dissolved in 100 ml solvent.

The average efflux time to generate the fibroin by the process according to the present invention is 594.08 seconds (inherent viscosity: 1.22 dL/g) while the average efflux time to generate the fibroin by the conventional dialysis process is 625.3 seconds (inherent viscosity: 1.27 dL/g). In view of the inherent viscosity obtained by the above experiment (corresponding to molecular weight of the fibroin), the molecular weight of the fibroin produced by the process of the invention does not have a significant difference with that of a conventional dialysis process.

Example 3

Preparation of Silk Fibroin by Adding Multivalent Acid Salt and Applying Shear Stress A solution of fibroin was prepared as described in Example 1 and yielded a solution containing 10 weight % of fibroin. The solution was diluted with de-ionized water (weight ratio 1:1). A $K_2SO_4$ solution was added to the diluted solution ($CaCl_2:K_2SO_4=1:1$ (mole)). After stirring to provide shear stress, the fibroin was precipitated. After being cleaned and dried, the fibroin and the calcium sulfate dihydrate powders ($CaSO_4.2H_2O$) were obtained. The calcium sulfate powders can be further used together with silk fibroin as bone substitute composites.

FIG. 1 shows the XRD results of the calcium sulfate dihydrate ($CaSO_4.2H_2O$), the fibroin along with the calcium sulfate dihydrate ($CaSO_4.2H_2O$) produced by the process according to the invention, and the potassium sulfate. The FIGURE confirms that the precipitate on the surface of the fibroin is calcium sulfate dihydrate ($CaSO_4.2H_2O$).

What is claimed is:

1. A dialysis-free process of producing a regenerated silk fibroin, comprising the steps of:
   (a) dissolving degummed silk fibroins in a salt containing solution to give a fibroin solution; and
   (b) applying a shear stress provided by a rotating speed ranging from 3,000 to 20,000 rpm to the fibroin solution for a time sufficient to make the silk fibroin precipitate, thereby producing a regenerated silk-fibroin.

2. The process of claim 1, wherein in step (b), the shear stress is provided by stirring, homogenizer or high speed homogenizer.

3. The process of claim 2, wherein in step (b) the shear stress is provided by a rotating speed ranging from 3,000 to 10,000 rpm.

4. The process of claim 2, wherein in step (b) a shear stress is provided by a rotating speed ranging from 5,000 to 10,000 rpm.

5. The process of claim 2, wherein in step (b) a shear stress is provided by a rotating speed ranging from 5,000 to 8,000 rpm.

6. The process of claim 1, wherein the salt containing solution in step (a) comprises an aqueous cupri-ethylenediamine solution, an aqueous ammonia solution of cupric hydroxide (Schweitzer's reagent), an aqueous alkaline solution of cupric hydroxide and glycerol (Roe's reagent), an aqueous lithium bromide solution, an aqueous solution of the chloride, nitrate or thiocyanate of calcium, magnesium or zinc, or an aqueous sodium thiocyanate solution.

7. The process of claim 6, wherein the salt containing solution is an aqueous solution of the chloride or nitrate of calcium or magnesium.

8. The process of claim 6, wherein the salt containing solution is an aqueous solution of $CaCl_2$.

9. The process of claim 6, wherein the salt containing solution is a solution of $CaCl_2/C_2H_5OH/H_2O$.

10. The process of claim 1, further comprising a degumming step of silk fibroin before step (a).

11. A dialysis-free process of producing a regenerated silk fibroin, comprising the steps of:
    (a) dissolving degummed silk fibroins in a salt containing solution to give a fibroin solution;
    (b') changing the solvent power of the fibroin solution; and
    (c) applying a shear stress to the fibroin solution for a time sufficient to make the silk fibroin precipitate, thereby producing a regenerated silk fibroin.

12. The process of claim 11, wherein in step (b'), the solvent power of the fibroin solution is changed by changing the proportion of the salts in the fibroin solution.

13. The process of claim 12, wherein the solvent power of the fibroin solution is changed by lowering the proportion of salts in the solution.

14. The process of claim 13, wherein the proportion of salts of the solution is lowered by adding multivalent acid ions to the fibroin solution.

15. The process of claim 14, wherein the multivalent acid ion is selected from the group consisting of $SO_4^{2-}$, $C_2O_4^{2-}$, $CO_3^{2-}$, and $PO_4^{3-}$.

16. The process of claim 14, wherein the multivalent acid ion is $SO_4^{2-}$ or $PO_4^{3-}$.

17. The process of claim 14, wherein the multivalent acid ion is derived from the salt containing $Na^+$ and/or $K^+$.

18. The process of claim 14, wherein the multivalent acid ion is derived from a salt selected from the group consisting of $K_2SO_4$, $KHSO_4$, $Na_2SO_4$, $NaHSO_4$, $Na_3PO_4$, $Na_2HPO_4$, $NaH_2PO_4$, $K_3PO_4$, $K_2HPO_4$, and $KH_2PO_4$.

19. The process of claim 11, wherein in step (b'), the solvent power of the fibroin solution is changed by increasing the proportion of water in the solution.

20. The process of claim 19, wherein the solution contains more than 90 wt % of water.

21. The process of claim 19, wherein the solution contains 0.1 to 3 wt %, 0.1 to 2 wt %, 0.1 to 1 wt % or 0.1 to 0.99 wt % of fibroin.

22. The process of claim 21, wherein the solution contains 0.1 to 0.99 wt % of fibroin.

23. The process of claim 21, wherein the solution contains 0.1 to 0.95 wt %, 0.5 to 0.95 wt %, 0.5 to 0.92 wt % or 0.6 to 0.9 wt % of fibroin.

24. The process of claim 11, wherein the salt containing solution of step (a) comprises an alcohol.

25. The process of claim 11, wherein the salt containing solution of step (a) comprises an alcohol and in step (b'), the solvent power of the fibroin solution is changed by increasing the proportion of alcohol in the solution.

26. The process of claim 11, further comprising a degumming step of silk fibroin before step (a).

27. The process of claim 11, wherein the salt containing solution of step (a) comprises an aqueous cupri-ethylenediamine solution, an aqueous ammonia solution of cupric hydroxide (Schweitzer's reagent), an aqueous alkaline solution of cupric hydroxide and glycerol (Roe's reagent), an aqueous lithium bromide solution, an aqueous solution of the chloride, nitrate or thiocyanate of calcium, magnesium or zinc, or an aqueous sodium thiocyanate solution.

28. The process of claim 27, wherein the salt containing solution of step (a) is an aqueous solution of the chloride or nitrate of calcium or magnesium.

29. The process of claim 27, wherein the salt containing solution of step (a) is an aqueous solution of $CaCl_2$.

30. The process of claim 27, wherein the salt containing solution of step (a) is a solution of $CaCl_2/C_2H_5OH/H_2O$.

31. The process of claim 27, wherein the salt containing solution in step (a) is a solution of $CaCl_2$ or $Ca(SCN)_2$.

* * * * *